United States Patent [19]

Simon et al.

[11] 3,957,607

[45] May 18, 1976

[54] PROCESS FOR THE PREPARATION OF LIPIDE SOLUBLE COMPLEXES OF CATIONS, APPLICATION OF THE PROCESS AND USE OF THE COMPLEXES

[75] Inventors: Wilhelm Simon, Oberembrach; Ernö Pretsch, Zurich, both of Switzerland

[73] Assignee: W. Moller Glasblaserei, Zurich, Switzerland

[22] Filed: Apr. 19, 1973

[21] Appl. No.: 352,634

[30] Foreign Application Priority Data

Apr. 24, 1972 Switzerland.................... 6064/72

[52] U.S. Cl.................... 204/180 P; 204/195 L; 204/195 M; 204/301; 260/2.2 R
[51] Int. Cl.²................ G01N 27/26; G01N 27/30; B01D 13/02
[58] Field of Search........... 204/195 L, 195 M, 301, 204/296, 180 P; 260/2.2 R

[56] References Cited
UNITED STATES PATENTS

| | | | |
|---|---|---|---|
| 3,378,505 | 4/1968 | Hay | 204/296 X |
| 3,497,424 | 2/1970 | Ross | 204/195 L X |
| 3,616,409 | 10/1971 | Tosteson | 204/195 L |
| 3,657,095 | 4/1972 | Tosteson | 204/195 L |
| 3,677,923 | 7/1972 | Bier | 204/301 X |
| 3,737,379 | 6/1973 | Tosteson | 204/195 L X |
| 3,753,887 | 8/1973 | Kedem et al. | 204/195 M |

OTHER PUBLICATIONS

Levins, "Barium Ion–Selective Electrode . . . Complex," 1971, Analytical Chem., Vol. 43, No. 8, pp. 1045–1047.

*Primary Examiner*—John H. Mack
*Assistant Examiner*—A. C. Prescott
*Attorney, Agent, or Firm*—Haseltine, Lake & Waters

[57] ABSTRACT

New lipide soluble complexes of cations like metal ions and ammonium ions are prepared by reacting an uncharged complex forming substance with the corresponding ions. Preferred uncharged complex forming substances are also new. The new lipide soluble complexes of cations have a wide field of application and those complexes, that is, the complex forming compounds can be used in membranes for the determination of the concentration of cations, like the ion sensitive members of measuring electrodes, or for the performance of an electro dialysis. Metal cations are generally insoluble in organic solvents and due to their solubility in organic solvents the new lipide soluble complexes of cations can be used in many fields of application, e.g. as catalysts for reactions which are performed in organic solvents.

6 Claims, No Drawings

PROCESS FOR THE PREPARATION OF LIPIDE SOLUBLE COMPLEXES OF CATIONS, APPLICATION OF THE PROCESS AND USE OF THE COMPLEXES

DESCRIPTION OF THE PRIOR ART

A great number of complexes are known which are formed by the reaction of an organic compound and a metal ion. Most of these complexes, however, are formed by a charged complex forming agent, for example, like the anion of a carboxylic acid, and the so formed complexes are generally not lipide soluble, even if the complex forming agent prior to its reaction with the metal ion had been soluble in organic solvents. Examples of such prior art complexes are the complexes of the tartaric acid or the acetoacetic acid with a great variety of different metal ions.

In recent times, however, (see W. E. Morf and W. Simon, Helvetica Chimica Acta Vol. 54, pages 2'683 - 2'704, 1971) lipide soluble complexes of ammonium and alkali metal ions and certain antibiotics of the valinomycin group, like the macrotetrolides, were discovered. The complex forming agent of these complexes is a material of biological origin and these complexes are formed from uncharged antibiotics and the corresponding monovalent cations. In those complexes, the non-solvatized monovalent ions are surrounded, that is, encased by the antibiotic and the polar groups of the antibiotic are directed to the interior part of the antibiotic, so that the metal ion is coordinated by 5 - 8 oxygen atoms. The surface of such complexes is lipophilic because the non-polar groups of the antibiotic are situated at the surface of the complex. This results in complexes of the antibiotics what are are highly soluble in lipides.

Furthermore, it is known that the above stated antibiotics can be used in ion sensitive membranes for the potentiometric determination of the concentration of alkali metal ions. Measuring electrodes of such antibiotics are similar to glass electrodes, the ion sensitive member of such electrodes, however, is not a glass membrane but rather a membrane which contains the antibiotics, e.g. a membrane containing a solution of such antibiotics.

SUMMARY OF THE INVENTION

One object of the present invention is the preparation of new complexes which consist of an uncharged complex forming agent and a cation and in which the uncharged complex forming agent is not of biological origin but is a synthetically prepared complex forming agent. The complexes are lipide soluble and the stability constant thereof is not influenced severely by the pH-value.

It has now been surprisingly found that new complexes of the above described kind, preferably complexes of metal ions, or ammonium ions can be prepared by using an uncharged organic compound or substance which can be either a compound having an open chain or a cyclic compound, provided that such compound has a certain arrangement of polar groups, e.g. groups containing oxygen or sulphur and non-polar groups, i.e. groups consisting essentially of hydro-carbon radicals.

The present invention concerns a process for the preparation of lipide soluble complexes of cations which comprises reacting an uncharged complex forming substance having the formula I

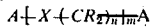  I in which
the group
A is a group terminating the chain which optionally comprises further groups X or wherein two groups Y when taken together with the group

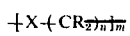

form a ring
X is a group having the formula

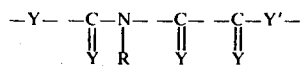

wherein in those groups Y and Y' are independent from each other oxygen or sulphur and wherein in the compounds of formula I at least one group X is other than an ether group and on the other hand at least one of the groups X is other than an ester group or acid amide group. Furthermore in those compounds of formula I which do not have a cyclic structure and in which the radicals X, which are ether groups alternate in the chain with radicals X having which are ester groups and wherein the radicals
R are hydrogen atoms or organic radicals or two radicals R together with the carbon atom to which they are bonded form a ring structure or a heterocyclic ring and
$m$ is an integer having a maximum value of 12 and
$n$ independently from each another are integers of from 1 – 15, the sum of all the members of the chain or the members of the ring which are formed by groups X or groups having the formula $-CR_2-$ is not more than 50 and form a complex with a metal ion or ammonium ion.
In the complex forming agents having the formula I
$m$ is preferably an integer of from 2 – 12. If the stochiometric ratio between the complex forming agent and the cation is 1 : 1 in the formed complex, then
$m$ of the complex forming agent of formula I is preferably an integer in the range of from 4 – 12.

In the compounds or substances of formula I the sum of all the members of the chain or the members of the ring which are formed by groups X or by groups having the formula $-CR_2-$ is preferably in the range of 10 – 50, e.g. in the range of 20 – 50. Furthermore, the complex forming agents having the formula I are preferably free of groups which are able to undergo an acid-base-reaction, i.e. free of —COOH groups, sulphonic acid groups and amino groups. The compounds of formula I can however comprise carbonic acid amide groups and thiocarbonic acid amide groups, as can be clearly seen from the above definition of the group X in formula I. In order to achieve good solubility in lipides, furthermore, the radical A and the radicals R are preferably free of hydroxy groups.

If the stochiometric ratio of cation to complex forming agents in the formed complexes is 1 : 1, then the complex forming agent shall comprise in its molecule preferably at least 4 groups X and often the complex forming agents have 6 or more groups X per molecule. If, however, the stochiometric ratio between the cation and the complex forming agent is higher than 1 : 1, then a complex formation can be achieved also with complex forming agents of formula I, which have less than 4 groups X and in which, accordingly, m has a value of below 4.

Preferred complex forming agents which are used for the preparation of the lipide soluble complexes have the following formula II

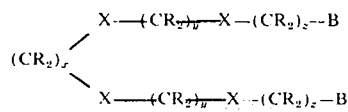

wherein in said formula II
x is an integer of from 1 – 6, the both y's are independent from each other and are integers of from 1 – 5 and
the both z's are independent from each other and are integers of rom 1 – 15 and
B is either a terminating group A or a group having the formula $$- X - (CR_2)_n - A$$

and optionally two groups A form together a member which closes the compound of formula II to a ring structure and wherein the number of all the members of the chain or the ring formed by groups X and groups having the formula $—CR_2—$ is not more than 50, and preferably not more than 42. In those groups having the formula $-CR_2-$ which are not directly bonded to the terminal group such as the ring closing group B, i.e. the groups $(CR_2)_x$ and $(CR_2)_y$ preferably all the radicals R are hydrogen atoms. Furthermore, those complex forming agents are especially preferred in which $x$ has a value of 2 and both y's are 1. A specially preferred structure of the complex forming agent accordingly has the following formula III

wherein
Y and Y' are independent from each other and are oxygen atoms or sulphur atoms and
B is a terminating group A or a group having the formula $$- (CR_2)_n - X - A$$

As already stated, for the compounds having the formula II and also in the above named compounds of formula III, both groups A, when taken together, can be a group which performs the ring closure of the compounds of formula III, i.e. both groups X are linked via the ring closing group.

Furthermore, it is to be noted that those compounds having the formula III are specially suited to use in the present invention when they have a symmetrical structure, i.e. Y and when Y' have the same meaning and both radicals X have as well the same meaning and also the both radicals B are either identical with each another or are the atoms which are necessary to perform the ring closure. Such compounds form especially stable complexes, preferably with ammonium ions, alkali metal ions and 2-valent and 3-valent ions like alkaline earth metal ions and in which both radicals Y and Y' are oxygen atoms and both groups X - B are acid amide groups. As it will be explained in more detail hereinafter, those compounds having the formula III, in which the groups —X—B are acid amide groups form generally more stable complexes than compounds having an equivalent structure, in which however the groups —X—B are for example ether groups or ester groups.

In the especially preferred complex forming agents having the formula III, accordingly, both radicals Y and Y' are oxygen atoms and both groups $$- X - B$$

are groups having the formula

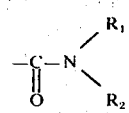

wherein
$R_1$ is an organic radical and
$R_2$ is a hydrogen atom or an organic radical or
the radicals $R_1$ and $R_2$ together with the nitrogen atom form a heterocyclic radical comprising optionally further hetero atoms, or the both radicals $R_1$ of the two groups of formula

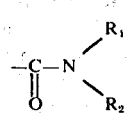

form together a group which closes the compounds of formula III to form a cyclic structure.

Especially preferred complex forming agents are those having the formula IV below

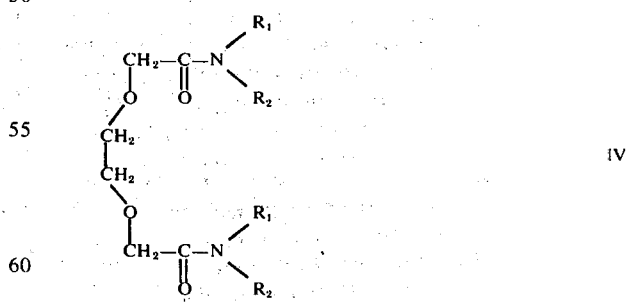

wherein
$R_1$ and $R_2$ have the above stated meaning.

With regard to the corresponding calcium complexes and barium complexes, i.e. complexes formed with $Ca^{++}$ and $Ba^{++}$ ions respectively, compounds which correspond to the compounds of the above stated formula IV but in which instead of both oxygen atoms forming the ether linkages, there are present further -CH$_2$-groups, such compounds either form no complexes at all or simply complexes which are less stable than complexes formed with the compounds having the formula IV. Also corresponding complexes in which there is an alkylene chain between the acid amide groups which does not comprise 6-CH$_2$-groups but rather a higher number or a lower number of —CH$_2$— groups either form no complexes at all or less stable complexes than the compounds having the formula IV. Furthermore, it is to be noted also that compounds of formula IV which do not have the unit $$-CH_2 - O - CH_2 - CH_2 - O - CH_2 -$$

but instead a unit having the formula $$- CH_2 - CH_2 - O - CH_2 - CH_2 - O - CH_2 - CH_2 -$$

possess less suitable complex forming activities.

In a specially preferred complex forming agent having the formula IV, the groups of the formula $$-\underset{\underset{O}{\|}}{C}-N\diagup^{R_1}_{\diagdown R_2}$$

can e.g. have the following structure $$-\underset{\underset{O}{\|}}{C}-N\diagup^{(CH_2)_a-Z-R_3}_{\diagdown R_2}$$

wherein
a is an integer of from 1 – 12 and
Z is a group having the formula $$-CH_2-, -O-, -COO- \text{ or } -\underset{\underset{R}{|}}{CON}-$$

R$_2$ is a hydrogen atom or a lower alkyl radical and
R$_3$ is either an alkyl-, cycloalkyl-, aralkyl-, aryl- or heterocyclic radical, which terminates both chains or both radicals R$_3$ of the stated terminal groups form together a group uniting both terminal groups to form a ring structure and which ring closing group is preferably an alkylene radical or an alkylene radical which is interrupted by further radicals Z.

Both acid amide groups of the compounds having the formula IV preferably have the same structure, i.e. R$_2$, and A and Z the same meaning in both acid amide groups and the radical R$_3$, furthermore, either has the same meaning in both of those groups or it is a group of symmetrical structure which closes both ends of the chain to form a ring structure. In the especially preferred compounds of the above stated structure which contain acid amide groups, both acid amide groups have the formula $$-N\diagup^{R_1}_{\diagdown R_2}$$

and which are either, when taken separately, groups having the formula

—NH—(CH$_2$)$_7$—COO—CH$_2$CH$_3$
—NH—(CH$_2$)$_3$—O—(CH$_2$)$_3$—CH$_3$

—NH—(CH$_2$)$_3$—N$\diagup\!\!\diagdown$(lactam ring with O)

—N(CH$_3$)—(CH$_2$)$_{10}$—COO—CH$_2$CH$_3$

—N(CH$_3$)—(CH$_2$)$_{10}$—COO—CH$_2$—⟨phenyl⟩

—N(CH$_3$)—(CH$_2$)$_{10}$—COO—C—(CH$_3$)$_3$

—N(CH$_3$)—(CH$_2$)$_6$—CH$_3$

—N(CH$_3$)—(CH$_2$)$_{11}$—COO—CH$_2$CH$_3$ $$-N\diagup^{CH_2CH_2CH_3}_{\diagdown CH_2-C(CH_3)_3}$$

or

— NH—(CH$_2$)$_9$—CH$_3$ or both groups together form a unit having the formula

—N(CH$_3$)—(CH$_2$)$_6$—N(CH$_3$)— or

—N(CH$_3$)(CH$_2$)$_6$—N(CH$_3$)—C(=O)—CH$_2$—O—(CH$_2$)$_2$—O—CH$_2$—C(=O)—N(CH$_3$)—(CH$_2$)$_6$N—

A further preferred complex forming agent having the formula IV is the following Alk—OOC—(CH$_2$)$_{10}$—N(CH$_3$)—C(=O)—CH$_2$—O—(CH$_2$)$_2$—O—CH$_2$—C(=O)—N(CH$_3$)—(CH$_2$)$_{10}$—COO—Alk wherein
Alk is an optionally substituted alkyl radical, preferably a methyl-, ethyl-, propyl-, tert.-butyl- or benzyl radical.

Complex forming agents of formula IV in which the radical R$_1$ is bonded via at least one CH$_2$-group to the nitrogen atom, show a good selectivity for calcium over other ions.

Further preferred complex forming agents having the formula IV are those in which in both groups having the formula

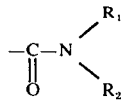

both radicals $R_1$ and $R_2$ when taken separately are aromatic radicals or heterocyclic radicals or when taken together with the nitrogen atom to which they are bonded are a heterocyclic radical comprising optionally further hetero atoms. The aromatic radicals can be phenyl radicals or substituted phenyl radicals and the heterocyclic radical can, for example be a morpholino radical or a carbazole radical. Some of these last mentioned complex forming agents have a good complex forming activity with respect to barium ions.

Examples of compounds which are somewhat similar to the specially preferred complex forming agents of formula IV and which however form either no complexes with calcium ions or have only a low complex forming activity with respect to calcium ions are compounds having the following structure: 1,1,3,3,6-dioxa-subericacid-bis-(1-(3-hydroxipropyl)-2-pyrrolidon)-esters having the formula

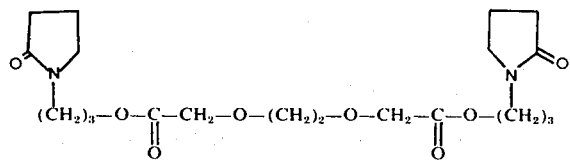

The above stated compounds do not form complexes with calcium ions because they have an ester group and no acid amide group. Also esters having the following formulae do not form complexes with calcium ions.

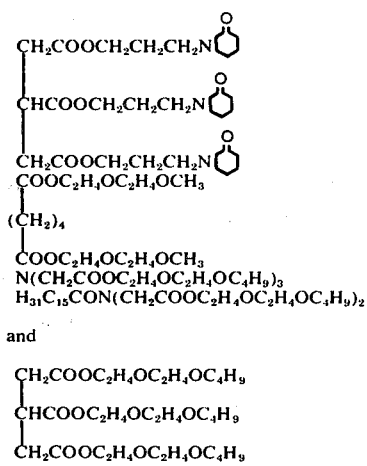

Compounds which differ from the compounds having the formula IV in that between the oxygen atom of the ether group and the acid amide group there are present more than one —$CH_2$—group, e.g. 2-$CH_2$-groups are less selective complex forming agents for calcium ions than the compounds having the formula IV. Some of these compounds, however, have a rather good selectivity with regard to barium ions.

Compounds which have a structure which is similar to those of formula IV but which, however, do not have an acid amide group but an ester group, generally have a higher complex forming activity for monovalent ions than for divalent ions. Examples for compounds of the last said case are those corresponding to formula III, in which Y and Y' are oxygen atoms and the groups -X-B are radicals having the formula

wherein
R is preferably a radical selected from the following groups:

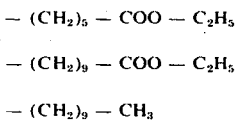

Such compounds form complexes with ammonium ions.

If in the compounds having the formulae I, II and III respectively, the groups X are ester groups, thioester groups, carbonic acid amide groups and thiocarbonic ester amide groups then of course the carbon atom of said groups has not to be bonded to a certain radical of the formula -$C_2$-. This means that, if for example in the compounds of formula II, in the unit $$-(CR_2)_y-X-(CR_2)_z-$$

the radical X is an ester group, this unit comprises groups having the formula

as well as groups having the formula

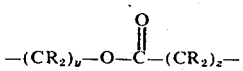

The complex forming agent of formula I and the complexes prepared according to the inventive process possess a sufficiently high selectivity so that they can be applied in electrodes having an ion sensitive membrane. For example, the preferred complexes formed with the complex forming agent of formula IV can be used for the determination of calcium ions and barium ions, using an electrode cell assembly which is similar to a glass electrode cell assembly in which, however, instead of a glass membrane, there is used a membrane which contains the complex forming material or the complex or a mixture of both. Such electrodes are somewhat generally like the electrode described in the U.S. Pat. No. 3,562,129, and which electrodes are ion specific with regard to alkali metals and contain antibiotics.

When ion selective electrodes are produced, the ion selective member of such electrodes can be prepared by impregnating a carrier material with the corresponding cation complex. It, however, is also possible to prepare an ion selective membrane which does not contain the cation complex itself, but only the complex forming agent and then under the working condition of the electrode, the complex forming agent is at least partially converted into the corresponding complex by bringing the electrode into contact with the cations which are contained either in the solution to be measured or in the buffer solution employed with the electrode. In the last case, the complex forming reaction accordingly occurs in the ion sensitive membrane itself.

A further object of the invention accordingly is the application of the inventive process for the determination of the concentration of cations or for the performance of an electro dialysis wherein the complex forming reaction between the compounds of formula I and the cation is performed in a membrane. A membrane which contains such a complex, however, cannot only be used as ion sensitive member of a measuring electrode for the determination of the concentrations of cations, but can also be used in a membrane for the separation of ions by electro dialysis. The ions the concentration of which shall be altered by such electro dialysis are preferably ions which are alkaline earth metals, alkali metals and ammonium ions.

In the above mentioned application of the inventive process, the membranes can be prepared as follows:

The complex forming agent is introduced into a membrane of polyvinyl chloride. Preferably, this is done by the following procedure: The polyvinyl chloride is dissolved in tetra-hydro furane and the complex forming agent of formula I as well as 1-octyloxy-2-nitrophenol which forms a solvent for calcium ions is added thereto.

The solution is cast to form a membrane and two aqueous solutions containing those ions which are to be tested as to the ion specifity of the membrane are separated from each another by said membrane. Then voltage is applied to the assembly and those ions for which the membrane is ion sensitive, are selectively transported via the membrane.

A compound having the formula IV, in which the groups of formula

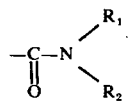

are groups having the following formula

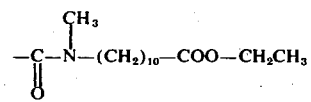

was tested. A membrane containing the compound was interposed between two aqueous solutions which contained calcium ions as well as other alkali metal ions and alkaline earth metal ions. The calcium ions were selectively transported via the membrane.

A membrane of the above stated kind or a membrane which contains as active ingredient a compound having the formula IV, in which in the above stated acid amide group $R_1$ is an n-propyl radical and $R_2$ is a radical having the formula $-CH_2-C(CH_3)_3$ can be also used as the ion sensitive membrane in an electrode for the determination of calcium ions. The selectivity of calcium over sodium of such kinds of electrodes is so high that they can be used for the determination of calcium ions in blood serum in which, as it is well known in the art, the concentration of sodium ions is far higher than the concentration of calcium ions.

The complexes prepared according to the inventive process are soluble in lipides and, therefore, such complexes, especially the corresponding complexes with metal ions, can be used as catalysts which exhibit the desired solubility in organic systems. For example, the calcium complex of the above stated complex forming agents used for the preparation of the membrane, can be used for such a purpose.

Further compounds of the general formula IV which are highly selective for calcium ions are those in which the acid amide groups, the group having the formula

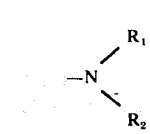

is one of the following groups:

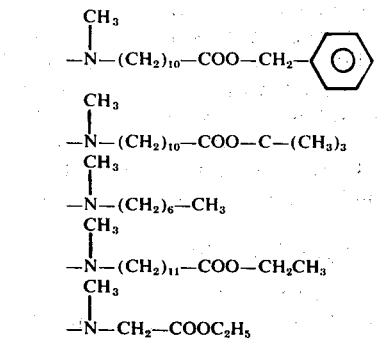

Compounds having the formula IV, and which contain the above stated group in the acid amide group and in which the radicals $R_1$ and $R_2$ are aromatic radicals or heterocyclic radicals or in which both radicals $R_1$ and $R_2$ together with the nitrogen atom to which they are bonded, form a heterocyclic ring system, and which optionally comprises further heteroatoms, generally possess a complex forming activity with regard to barium ions. As special compounds of the last mentioned kind, there are those of formula IV in which in the both amide groups of the given formula, the radicals $R_1$ and $R_2$ are unsubstituted phenyl radicals or the radicals $R_1$ and $R_2$ form together with the nitrogen atom to which they are bonded, a carbazole radical.

The compounds used for the preparation of the complexes according to the inventive process and having the formula I and the preferred compounds of the formulae II, III and IV are generally new compounds. They, however, can be prepared according to processes which are as such known in the organic chemistry.

There follows descriptions of preparations methods for making special compounds of formula IV and which also the preparation of one compound which does not correspond to formula IV and was prepared for comparative test purposes.

PREPARATION I

Preparation of 3,15,18,30-tetraoxa-4,13,20,29-tetraoxo-12,21-diazadotriacontane

The compound corresponds to the following formula IV

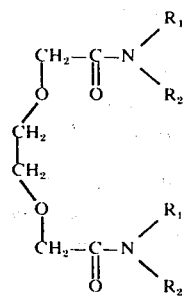

and in this formula both radicals $R_2$ are hydrogen atoms and both radicals $R_1$ are groups having the formula $-(CH_2)_7-COO-C_2H_5$.

a. Preparation of 8-amino-caprylic acid ethylester 1.5 grams (9.43 millimoles) of 8-amino-caprylic acid (Fluka, puriss.) were suspended in ethanol and gaseous HCl was introduced into the suspension until the acid had dissolved. The solution was refluxed for 48 hours and, thereafter, concentrated in vacuo using a rotating evaporator. 0.1 molar sodium hydroxide was added to the residue and an extraction with chloroform performed. A yield of 1.46 grams (7.8 millimoles) of the ethyl ester of the 8-amino-caprylic acid was obtained (83% of theory).

$^1$H-NMR: (-COOCH$_2$CH$_3$) 4.2/q; 1.2/t b. Preparation of 3,15,18,30-tetraoxa-4,13,20,29-tetraoxo-12,21-diazadotriacontane The preparation of triglycolic acid dichloride starting from triethylene glycol was described in the doctoral thesis of J. P. Sauvage, Louis Pasteur University, Strassbourg, 1971. According to that process, triethylene glycol is oxidized to form the corresponding dicarboxylic acid and the acid is reacted with oxalyl chloride to form the dichloride of the triglycolic acid. In the present preparation, however, thionyl chloride was used instead of oxalyl chloride.

0.79 gram (4.24 millimoles) of ethyl 8-aminocaprylate (ethyl ester of the 8-amino caprylic acid) was dissolved in 100 ml pyridine. The solution was stirred and 0.46 gram (0.11 millimoles) of triglycolic acid dichloride dissolved in 20 ml of ether was added slowly thereto. The reaction mixture was stirred for an additional 17 hours at room temperature and thereafter concentrated. The remaining pyridine was stripped off two times with benzene as an azeotropic mixture. The pyiridinium hydrochloride was removed by extracting the material twice with water/ether mixture in a separatory funnel. The product was recrystallized from acetone. 0.70 gram (1.35 millimoles, 64 % of theory) of the desired product were obtained.

IR: 3,470, 1,720, 1,660, 1,530
$^1$H-NMR (in chloroform-d)
1.25/6, CH$_3$-1; 2.3/br, CH$_2$-5;
3.3/br, CH$_2$-11; 3.75/s, CH$_2$-16;
4.0/s, CH$_2$-14; 4.1/q, CH$_2$-2;
7.66/br,NH-9
Mass spectrometry: 516 (C$_{26}$H$_{48}$N$_2$O$_8$)
Elemental analysis:
calculated for C$_{26}$H$_{48}$N$_2$O$_8$:
 C 60.44 % H 9.36 % N 5.42 %
found: C 60.74 % H 9.23 % N 5.95 %

Preparation II

Preparation of 5,12,15,22-tetraoxa-9,18-diaza-10,17-dioxo-hexacosane

This compound corresponds to formula IV, given in preparation I and in which in the acid amide groups of that formula both radicals $R_2$ are hydrogen atoms and both radicals $R_1$ are groups having the structure

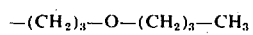
$-(CH_2)_3-O-(CH_2)_3-CH_3$ 800 mg (6.1 millimoles) of 3-butyloxy-1-propylamine (Fluka, purum) were added to 12 ml pyridine and then 613 mg (2.85 millimoles) triglycolic acid dichloride dissolved in some diethyl ether were added thereto. The mixture was stirred at room temperature for 24 hours and then concentrated and the pyridinium hydrochloride removed by an extraction with water/ether mixture, the extraction being performed in a separatory funnel. The crude product was submitted twice to a micro-distillation (bulb tube, 145° C, 0.01 mm Hg) and the resulting uncoloured liquid crystallized from acetone. 406 mg (1.0 millimoles) of the desired product corresponding to 32% of theory were obtained.

IR-spectrometry:
3,460, 3,400, 1,680, 1,520, 1,110
$^1$H-NMR (in dimethylsulfoxide-d$_6$):
0.9/t, CH$_3$-1; 3.22/q, CH$_2$-8;
3.45/t and 3.48/t, CH$_2$-4,
CH$_2$-6; 3.63/s, CH$_2$-13; 3.90/s,
CH$_2$-11; 6.65/br, NH
Mass spectrometry:
404 (C$_{20}$H$_{40}$N$_2$O$_6$)
Elemental analysis:
calculated for C$_{20}$H$_{40}$N$_2$O$_6$:
 C 59.38% H 9.97% N 6.93%
found:
 C 59.13% H 9.93% N 6.82%

Preparation III

Preparation of 1,16-di(N-pyrrolidone(2)-yl)4,13-diaza-5,12-dioxo-7,10-dioxahexadecane This compound corresponds to formula IV of preparation I and in which in the acid amide groups both radicals $R_2$ are hydrogen atoms and both radicals $R_1$ are groups of the structure

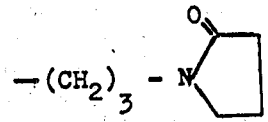

1-(3-aminopropyl)-2-pyrrolidone (Fluka, purum) was purified by distillation over a vigreux-column (112° -114° C, 0.5 mm Hg). 491 mg (3.46 millimoles) of this amine were mixed with 12 ml pyridine and 332 mg (1.54 millimoles) triglycolic acid dichloride mixed with a little ether were added to the mixture which was then stirred for 20 hours at room temperature. Thereafter the solution was concentrated, mixed with water and extracted with chloroform. The brown oil which resulted after the evaporation was submitted to a microdistillation (bulb tube 160°C, 0.02 mm Hg). A yield of 56 mg (0.13 millimoles) of a slightly yellow oil was obtained (9% of theory).
IR-spectrometry:
 3,600 bis 3,200, 1,680, 1,660
$^1$H-NMR (in chloroform-d):
 3.8/s, $CH_2$-8; 4.05/s, $CH_2$-6; 7.55/br, NH-4
Mass spectrometry: 426 ($C_{20}H_{34}N_4O_6$)
Elemental analysis:
 calculated for $C_{20}H_{34}N_4O_6$:
  C 56.32% H 8.04% N 13.14%
 found:
  C 56.79% H 8.19% N 12.57%

Preparation IV

Preparation of 15,24-dimethyl-3,18,21,36-tetraoxa-4,16,23,35-tetraoxo-15,24-diazaoctatriacontane This compound corresponds to formula IV, given in preparation I, and in which both radicals $R_2$ are methyl groups and both radicals $R_1$ are groups having the structure

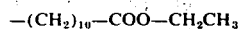

11-methylamino-undecanoic acid (Fluka, purum) was esterified to the corresponding ethyl ester using the method described in preparation I. 2.49 grams (10.26 millimoles) the said ethyl 11-methylamino-undecanoate were added to 50 ml pyridine. 1.12 grams (5.2 millimoles) of triglycolic acid dichloride, dissolved in a little ether were added drop by drop to the ester. Then, stirring of the mixture was continued for 16 hours more at room temperature and the pyridine was distilled off. The residue was dissolved in water and extracted with ether. From the ether layer a brownish oil was obtained. A part of the oil was purified using a silical gel column (Merck, 70 – 325 mesh ASTM), using acetone as the eluant. The chromatography procedure resulted in a rather large loss of product of about 50%.
IR-spectrometry:
 1,725, 1,650
$^1$H-NMR (in chloroform-d):
 1.25/t, $CH_3$-1, 2.30/br, $CH_2$-5;
 2.95/s und 2.97/s, N-$CH_3$; 3.35/br,
 $CH_2$-14; 3.88/s $CH_2$-19; 4.20/q,
 $CH_2$-2; 4.22/s, $CH_2$-17
$^{13}$C-NMR (in chloroform-d):
 14.3, $CH_3$-1; 25.1, $CH_2$-6; 26.9, $CH_2$-12
 27.2/28.5, $CH_2$-13; H 33.1/34.4; N-$CH_3$; 34.4, $CH_2$-5;
 48.0/49.1, $CH_2$-14; 60.0, $CH_2$-2; 70.2/70.5, $CH_2$-17,
 70.6, $CH_2$-19; 168.9,
 C-16; 173.6, C-4
Mass spectrometry: 628 ($C_{34}H_{64}H_2O_8$)
Elemental analysis:
 calculated for $C_{34}H_{64}N_2O_8$:
  C 64.93% H 10.26% N 4.45%
 found:
  C 64.70% H 10.31% N 4.35%

Preparation V

Preparation of 1,36-diphenyl-14,23-dimethyl-2,17,20,35-tetraoxa-3,15,22,34-tetraoxa-14,23-diazahexatriacontane This compound corresponds to formula IV, stated in preparation I, and in which both radicals $R_2$ are methyl radicals and both radicals $R_1$ are groups having the structure

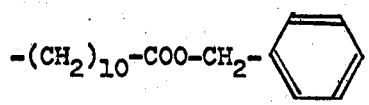

a. Saponification of the product produced according to preparation IV 199 mg (0.32 millimoles) of 15,24-dimethyl-3,18,21,36-tetraoxa-4,16,23,35-tetraoxa-15,24-diazaoctatriacontane were added to 5 ml ethanol and 5 ml aqueous saturated potassium carbonate solution and the mixture was refluxed for 3 hours. Two phases were formed. The ethanol layer was concentrated, then water was added and by the addition of acid, the pH was brought to a value of 2. Then, the product was extracted with ether. The product was recrystallized in acetone and a yield of 86 mg (0.15 millimoles) of the diacid, corresponding to 47% of theory was achieved.
Elemental analysis:
 calculated for $C_{30}H_{56}N_2O_8$:
  C 62.91% H 9.86% N 4.89%
  found: C 62.73% H 9.72% N 4.66% b. Preparation of the 1,36-diphenyl-14,23-dimethyl-2,17,20,35-tetraoxa-3,15,22,34-tetraoxo-14,23-diaza-hexatriacontane 73 mg (0.13 millimoles) of the names diacid were added to 1 ml of chloroform which was immediately before filtered through Alox (activity I, neutral) and 142.6 mg (0.53 millimoles) of dimethylformamide dibenzylacetal (Fluka puriss.) were added thereto in a nitrogen atmosphere. The mixture was left for 100 hours at room temperature in the nitrogen atmosphere. Then, ether was added, and the solution was washed twice with 2N hydrochloric acid, once with water, twice with a saturated aqueous solution of $NaHCO_3$ and finally were three times with water. The product was purified by thick layer-chromatography (solvent = acetone). 40 mg (0.053 millimoles of the desired product were recovered, corresponding to 41% of theory.
$^1$H-NMR (in chloroform-d):
 2.30br, $CH_2$-4; 2.95/s und 2.97/s,
 N-$CH_3$; 3.30/br, $CH_2$-13; 3.85/s,
 $CH_2$-18; 4.20/s, $CH_2$-16; 5.1/s, $CH_2$-1;
 7.35/s, Phenyl-1
Mass spectrometry: 752 ($C_{44}H_{68}N_2O_8$)
Elemental analysis:
 calculated for $C_{44}H_{684}N_2O_8$:
  C 70.18% H 9.10% N 3.72; %
  found: C 70.04% H 9.04% N 3.50%

Preparation VI

Preparation of 2,2,15,24,36,36-hexamethyl-3,18,21,36-tetraoxa-4,16,23,35-tetraoxo-15,24diazaoctatriacontane This compound corresponds to formula IV, stated in preparation I, and in which in the acid amide group both radicals $R_2$ are methyl groups and both radicals $R_1$ groups having the structure

$-(CH_2)_{10}-COO-C(CH_3)_3$ 90 mg (0.15 millimoles) of the diacid from preparation Va were added to 1.2 ml of chloroform, which was immediately before made water-free by filtration through Alox (activity I, neutral), and adding to the mixture under a nitrogen atmosphere 102 mg (0.50 millimoles) of dimethylformamide-ditert.-butylacetal. The mixture was left 100 hours at room temperature under the nitrogen atmosphere. The volatile by-products formed were removed using a rotating evaporator and the remainder was dissolved in ether and washed twice with 2N hydrochloric acid, once with water, twice with saturated $NaHCO_3$-solution and three times with water.

A yield of 21 mg (0.031 millimoles) of the desired product, corresponding to 21% of theory was recovered.

IR-spectrometry; 1,725, 1,650
$^1$H-NMR (in chloroform-d):
1.45/s, $CH_3$-1, 2-$CH_3$; 2.30/br, $CH_2$-5; 2.95/s und 2.97/s, N-$CH_3$; 3.35/br, $CH_2$-14; 3.75/s, $CH_2$-19; 4.20/s, $CH_2$-17

Mass spectrometry: 628 ($M^+$-$C_4H_8$)
Elemental analysis:
calculated for $C_{38}H_{72}N_2O_8$:
C 66.63% H 10.68% N 4.09%
found: C 66.70% H 10.56% N 4.11%

Preparation VII

Preparation of 8,17-dimethyl-8,17-diaza-9,16-dioxo-11,14-dioxa-tetracosane

This compound corresponds to formula IV, stated in preparation I and in which both radicals $R_2$ are methyl radicals and both radicals $R_1$ are groups having the structure

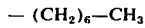
$-(CH_2)_6-CH_3$ 603 mg (4.67 millimoles) N-heptyl-methylamine (Fluka, purum) were mixed with 20 ml pyridine and 505 mg (2.35 millimoles) of triglycolic acid dichloride dissolved in a little ether were added thereto. The mixture was stirred for 18 hours at room temperature, and thereafter concentrated. The pyridine was completely removed by submitting the mixture to an azeoctropic distillation with benzene. The resulting product was dissolved in ether and washed with water. Then, it was purified by a thick layer-chromatography using silicagel plates and a mixture of three parts acetone plus one part methanol as solvent. 400 mg (1.00 millimoles) of the desired product were recovered, corresponding to 42% of theory.

IR-spectrometry: 1,650
$^1$H-NMR (in chloroform-d):
0.85/t, $CH_3$-1; 2.97/s und 2.99/s, N-$CH_3$; 3.40/br, $CH_2$-7; 3.80/s, $CH_2$-12; 4.25/s, $CH_2$-10.

$^{13}$C-NMR (in chloroform-d):
14.1, $CH_3$-1; 22.7, $CH_2$-2; 26.9, $CH_2$-5; 27.2 und 28.6, $CH_2$-6; 29.2, $CH_2$-4; 31.9, $CH_2$-3; 33.1 und 34.3 N-$CH_3$; 48.0 und 49.2, $CH_2$-7; 70.2 und 70.6, $CH_2$-17; 70.6, $CH_2$-19; 168.8, C-9.

Mass spectrometry: 400 ($C_{22}H_{44}O_4N_2$)
Elemental analysis:
calculated for $C_{22}H_{44}O_4N_2$:
C 65.96% H 11.07% N 6.99%
found: C 65.37% H 11.00% N 6.73%

Preparation VIII

Preparation of 11,20-diaza-12,19-dioxo-14,17-dioxa-triacontane

This compound corresponds to formula IV, stated in preparation I, and in which both radicals $R_2$ are hydrogen atoms and both radicals $R_1$ are n-decyl radicals having the structure

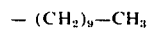
$-(CH_2)_9-CH_3$ 195 mg (1.24 millimoles) n-decylamine (Fluka, puriss.) were mixed with 10 ml pyridine and 149 mg (0.69 millimoles) of triglycolic acid dichloride, dissolved in ether were added thereto. The mixture was stirred for 96 hours at room temperature and then the pyridine was evaporated. The remaining product was dissolved in water and extracted with ether. Thereafter, it was recrystallized three times from acetone.

A yield of 190 mg (0.42 millimoles) of the desired product, corresponding to 60% of theory, was obtained.

IR-spectrometry:
3,400, 1,670
$^1$H-NMR (in chloroform-d):
0.9/t, $CH_3$-1; 3.25/q, $CH_2$-10; 3.70/s, $CH_2$-15; 4.0/s, $CH_2$-13; 6.70/br, NH-11

Elemental analysis:
calculated for $C_{26}H_{52}N_2O_4$:
C 68.37% H 11.48% N 6.13%
found: C 68.32% H 11.38% N 6.02%

Preparation IX

Preparation of 1,1,10,10-tetraphenyl-1,10-diaza-2,9-dioxo-4,7-dioxadecane

This compound corresponds to formula IV of preparation I and in which in the acid amide groups both radicals $R_1$ and both radicals $R_2$ are unsubstituted phenyl radicals.

2.0 grams (11.8 millimoles) of diphenylamine (Fluka puriss.) were mixed with 20 ml of benzene and 20 ml of pyridine and 1.07 grams (5.0 millimoles) of triglycolic acid dichloride were added thereto. This solution was stirred for 24 hours at room temperature, concentrated and mixed with chloroform and then treated in a separatory funnel with 0.1 N sodium hydroxide. The chloroform layer was separated and stripped of and the residue recrystallized twice, then dissolved in a mixture of ethanol and acetone and precipitated with ether.

1.12 grams (2.3 millimoles) of the desired product were obtained, corresponding to 47% of theory.

The product had a melting point of 95 - 97°C.

IR-spectrometry:
1,680, 1,590, 1,480
$^1$H-NMR (in chloroform-d):
3.7/s, $CH_2$-5; 4.05/s, $CH_2$-3; 7.30/s, Phenyl-1

¹³C-NMR (in chloroform-d):
70.2, $CH_2$-3; 71.0, $CH_2$-5; 127.1, CH-2' and CH-3'; 129.3, CH-4'; 141.7, C-1'; 169.1, C-2

Mass spectrometry:
480 ($C_{30}H_{28}O_4N_2$)

Elemental analysis:
calculated for $C_{30}H_{28}O_4N_2$:
C 74.98% H 5.87% N 5.83%
found:
C 75.00% H 6.00% N 5.93%

Preparation X

Preparation of 1,10-dimethyl-1,10-diaza-2,9-dioxo-4,7-dioxa-cyclohexadecane

This compound corresponds to formula IV, stated in preparation I, but in which both radicals $R_2$ are methyl groups and both radicals $R_1$ form together a hexamethylene radical, i.e. a group having the structure $$-(CH_2)_6-$$

1.6-bis-(methylamino)-hexane (Fluka, pract.) was distilled at 50° C (0,3 mm Hg) using a Vigreux-column. A 3-necked flask was equipped with a good stirring device and charged with 200 ml of dry benzene. Within 6 hours, 2.34 grams (10.93 millimoles) of triglycolic acid dichloride dissolved in 300 ml benzene and 2.96 grams (20.52 millimoles) of 1,6-bis-(methylamino)-hexane dissolved in 300 ml benzene were each added drop by drop to the contents of the 3-necked flask.

Stirring was continued for one more hour at room temperature and then the solution was concentrated. Ethyl acetate was added and the solid product separated by centrifuging. A part of the product dissolved in the ethyl acetate was purified by thicklayer-chromatography using methanol as solvent.

IR-spectrometry: 1,640

¹H-NMR (in methanol-$d_4$):
2.90/s and 3.00/s, N-$CH_3$;
3.3/m, $CH_2$-11; 3.65/s and 3.70/s, $CH_2$-5;
4.18/s and 4.28/s, $CH_2$-3

¹³C-NMR (in methanol-$d_4$):
24.9 - 28.2, $CH_2$-12, $CH_2$-13 (5 signals);
32.2, 32.7, 34.9, N-$CH_3$; 46.7, 48.3,
49.5, $CH_2$-11; 70.8 - 72.1, $CH_2$-3,
$CH_2$-5 (5 signals); 169.8 and 170.4, C-2

The product consists of at least 3 conformations because of the slow exchange (rotations) several signals per C-atom can be noticed.

Mass spectrometry:
286 ($C_{14}H_{26}N_2O_4$)

Elemental analysis:
calculated for $C_{14}H_{26}N_2O_4$:
C 58.72% H 9.15% N 9.78%
found:
C 58.42% H 9.26% N 9.49%

Preparation XI

Preparation of 16,25-dimethyl-3,38-dioxa-4,17,24,37-tetraoxo-16,25-diaza-tetracontane This compound was prepared for comparison and the difference between this compound and the compounds of formula IV, set forth in preparation I is that each of oxygen atom of the both ether groups of the compounds of formula IV is substituted by a -$CH_2$-group. In the acid amide group of this compound, both radicals $R_2$ are methyl radicals and both radicals $R_1$ are groups having the structure $$-(CH_2)_{11}-COO-C_2H_5$$

723 grams (2.81 millimoles) of 12-methylaminolauric acid ethylester were prepared according to the esterification procedure described in preparation I and this ester was mixed with 50 ml of pyridine, stirred vigorously and reacted with 300 mg (1.40 millimoles) of suberic acid dichloride (Fluka purum) dissolved in a little ether. The stirring was continued for 24 hours at room temperature and then the pyridine was stripped off, the residue mixed with water and extracted with ether. The ether layer was concentrated, the residue dissolved in chloroform and washed with 0.1 N sodium hydroxide. A part of said product was purified by thick layer-chromatography using a mixture of 2 parts acetone and one part chloroform as solvent.

IR-spectrometry:
1,720, 1,640

¹H-NMR (in chloroform-d):
1.25/t, $CH_3$-1; 2.30/br, $CH_2$-5
and $CH_2$-18; 2.92/s and 2.97/s,
N-$CH_3$; 3.30/br, $CH_2$-15; 4.15/q,
$CH_2$-2

Mass spectrometry:
652 ($C_{38}H_{72}N_2O_6$)

Elemental analysis:
calculated for $C_{38}H_{72}N_2O_6$:
C 69.89% H 11.11% N 4.29%
found:
C 69.46% H 11.11% N 4.11%

EXAMPLE 1

The barium complex of the compound prepared according to preparation IX was produced.

300 mg (0.625 millimoles) of 1,1,10,10-tetraphenyl-1,10-diaza-2,9-dioxo-4,7-dioxa-decane were dissolved in 5 ml of methanol by warming the mixture slightly. The solution was mixed with a warm solution of barium rhodanide in methanol, which contains 20 mg (0.375 millimoles) of Ba(SCN)$_2$ in 5 ml of methanol. It was cooled and from the solution white crystals of the desired complex precipitated.

EXAMPLE 2

The compound prepared according to preparation VII was reacted with calcium modanide according to the process described in example 1. The corresponding calcium complex was obtained.

What is claimed is:

1. A process for the determination of the concentration of cations and performing electrodialysis using a membrane made by the process which comprises reacting in said membrane an uncharged complex forming substance which forms lipide soluble complexes with the cations whose concentrations are to be determined, said uncharged complex forming substance having the formula I

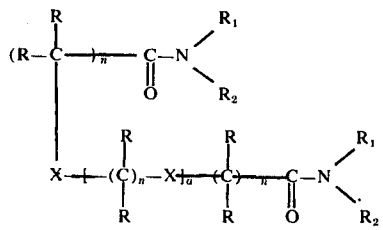

in which X is selected from the group consisting of

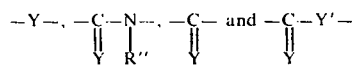

wherein R'' is selected from the group consisting of hydrogen and organic radicals, Y and Y' are independent from each other and are selected from the group consisting of oxygen and sulphur atoms and wherein in the compounds of formula I at least one X is other than an ester an an acid amide group, and wherein the radicals R are selected from the group consisting of hydrogen and organic radicals wherein two radicals R can form, together with the carbon atom and atoms to which they are bonded, a ring-structure which may be a heterocyclic ring; $R_1$ and $R_2$ are selected from the group consisting of hydrogen and organic radicals, and when $R_1$ is an organic radical, $R_2$ is selected from the group consisting of hydrogen and organic radicals, and wherein when $R_1$ and $R_2$ together with the nitrogen atom of a group

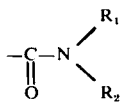

of formula I form a heterocyclic radical and when wherein $R_1$ of the two groups

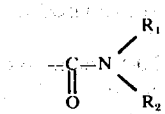

of the formula I form together a group which closes the substance of formula I to form a cyclic structure, a is a value selected from 0 and in integer having a maximum value of 11 and the n's are independent from each other and are integers of from 1 – 15 and the sum of all the members of the chain, when the substance of formula I is a straight chain and when the compound of the formula I has a cyclic structure, the members of the ring being formed by X and groups

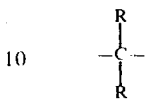

is not more than 50 with a cation which is a metal or ammonium ion.

2. A process as defined in claim 1 including using the cation complex formed with uncomplexed complex forming substance having the formula I as components of an ion sensitive member of a measuring electrode and determining the cation concentration with said electrode.

3. A process as defined in claim 1 including using the cation complex formed with uncomplexed complex forming substance having the formula I as components of an ion sensitive member of a measuring electrode and wherein the cation which forms the complex is provided by the presence of the cation in a solution selected from (1) the buffer solution filling said electrode and (2) the solution of which the cation concentration is being determined with said electrode.

4. A process as defined in claim 1 wherein the cation is selected from the group consisting of $Ca^{++}$ and $Ba^{++}$.

5. A process as defined in claim 1 wherein material selected from the group consisting of the uncharged complex forming substance having the formula I, the complex thereof with a cation which is a metal or ammonium ion and a mixture of said uncharged complex forming substance and the complex thereof with a cation which a metal or ammonium ion is employed in an electrodialysis membrane and the cations are separated by electrodialysis.

6. A process as defined in claim 1 wherein the cations are selected from the group consisting of alkaline earth metal ions, alkali metal ions and ammonium ions and are separated by electrodialysis.

* * * * *